United States Patent [19]

Kidani et al.

[11] Patent Number: 4,879,379

[45] Date of Patent: Nov. 7, 1989

[54] PLATINUM-STEROID COMPLEXES

[75] Inventors: Yoshinori Kidani, Mataho Kodan Jutaku 2-718, 1, Mataho-cho 2-chome, Nishi-ku; Masahide Noji, both of Nagoya, Japan

[73] Assignee: Yoshinori Kidani, Aichi, Japan

[21] Appl. No.: 99,298

[22] Filed: Sep. 17, 1987

[30] Foreign Application Priority Data

Sep. 19, 1986 [JP] Japan .................. 61-219428

[51] Int. Cl.$^4$ .............................. C07J 1/00
[52] U.S. Cl. ..................... 540/3; 260/397.4; 556/137
[58] Field of Search ............ 556/137; 540/3; 260/397.4

[56] References Cited

U.S. PATENT DOCUMENTS

| | | | |
|---|---|---|---|
| 2,959,584 | 11/1960 | Fried | 540/3 |
| 3,492,293 | 1/1970 | Fried | 540/3 |
| 4,115,418 | 9/1978 | Gale et al. | 556/137 |
| 4,169,846 | 10/1979 | Kidani et al. | 424/287 |
| 4,196,204 | 4/1980 | Petzoldt et al. | 260/397.4 |
| 4,200,583 | 4/1980 | Kidani et al. | 424/287 |
| 4,224,320 | 9/1980 | Dahl et al. | 260/397.4 |
| 4,359,425 | 11/1982 | Totani et al. | 556/137 |
| 4,482,494 | 11/1984 | Boor et al. | 260/397.4 |
| 4,482,706 | 11/1984 | Tomimatsu et al. | 260/397.4 |
| 4,670,427 | 6/1987 | Annen et al. | 260/397.4 |
| 4,678,609 | 7/1987 | Engels | 260/397.4 |
| 4,710,577 | 12/1987 | Kidani et al. | 556/137 |

FOREIGN PATENT DOCUMENTS

| | | | |
|---|---|---|---|
| 0147926 | 10/1983 | European Pat. Off. | 424/287 |
| 0237450 | 9/1987 | European Pat. Off. | 556/137 |
| 55-35013 | 3/1980 | Japan | 424/287 |
| 5130992 | 10/1980 | Japan | 424/287 |
| 59-21697 | 2/1984 | Japan | 424/287 |
| 60-34982 | 2/1985 | Japan | 424/287 |
| 60-87295 | 5/1985 | Japan | 424/287 |
| 60-97991 | 5/1985 | Japan | 424/287 |
| 62-59289 | 3/1987 | Japan | 424/287 |

Primary Examiner—Anthony McFarlane
Attorney, Agent, or Firm—Larson and Taylor

[57] ABSTRACT

Novel platinum(II)-steroid complexes are now provided, which exhibit antitumor activities as shown by tests on mouse leukemia, L-1210 cells in mice. These novel platinum(II)-steroid complexes contain a 1,2-cyclohexanediamine, a 2-(aminomethyl)cyclohexylamine, an ethylenediamine or $NH_3$—groups as a ligand or ligands.

9 Claims, 12 Drawing Sheets

FIG. I

PLATINUM-STEROID COMPLEXES

SUMMARY OF THE INVENTION

This invention relates to novel platinum(II)-steroid complexes, which contain a 1,2-cyclohexanediamine, a 2-(aminomethyl)cyclohexylamine, an ethylenediamine or $NH_3$— groups as a ligand or ligands. The platinum-(II)-steroid complexes exhibit antitumor activities as demonstrated by tests on mouse leukemia, L-1210 cells in mice.

BACKGROUND OF THE INVENTION

In recent years, a number of platinum(II) complexes, including well-known cisplatin, have been synthesized and have been reported to have antitumor activity. We, the present inventors, have synthesized some platinum-(II) complexes, as disclosed, for example, in Japanese Patent Application First Publn. (KOKAI) Nos. 31648/78. 35013/80, 130992/80, 103192/81, 156416/82, 16895/82, 21697/84, 34982/85, 34983/85, 97991/85, 109521/85 and 59289/87; Japanese Patent Application Second Publn. (KOKOKU) Nos. 29957/83, 34958/85 and 41077/85 as well as U.S. Pat. Nos. 4,169,846; 4,200,583; 4,256,652; 4,255,347; 4,551,524 and U.S. patent appln. Ser. No. 637,463 and European Patent Nos. 1126 and 8936, European Patent Appln. Nos. 83 303659.3 and 84 305304.2.

We have also synthesized some organoplatinum(IV) complexes, as disclosed, for example, in Japanese Patent Application First Publication (KOKAI) Nos. 87295/85 and 109521/85; Japanese Patent Appln. No. 48625/86, as well as U.S. patent appln. Ser. No. 020,893 and European Patent Appln. No. 87 420061.1.

Although a variety of platinum complexes as above has been known to date, there is still a standing demand for a novel compound having more excellent antitumor activities. It is a primary object of this invention to provide such a novel antitumor platinum compound.

DETAILED DESCRIPTION OF THE INVENTION

Now, we, the present inventors, have succeeded in synthesizing new organo-platinum(II) compounds, more particularly, platinum(II)-steroid complexes of formula (I) given below, and we have also found that these new platinum(II)-steroid complexes now synthesized exhibit an antitumor activity as demonstrated by the test against mouse leukemia L-1210.

According to this invention, therefore, there is provided a new platinum(II)-steroid complex represented by the general formula (I)

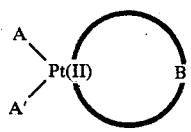

(I)

wherein A and A' taken together form a 1,2-cyclohexanediamine ligand of the formula:

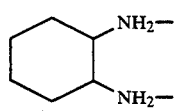

where the 1- and 2-amino groups have a configuration selected from cis-, trans-l- and trans-d-, relative to the cyclohexane ring; or A and A' taken together form a 2-(aminomethyl)cyclohexylamine ligand of the formula:

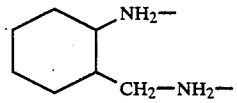

where the 1-amino group and 2-aminomethyl group have a configuration selected from cis-l-, cis-d-, trans-l- and trans-d-, or a mixture thereof, relative to the cyclohexane ring; or A and A' taken together form an ethylenediamine ligand of the formula:

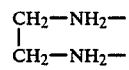

or A and A' each denote $NH_3$—, and B denotes a steroid compound which coordinates the platinum(II) atom, or a nitrate of the platinum(II)-steroid complex of the formula (I).

With the platinum(II)-steroid complex of the formula (I) according to this invention where the moiety

is the 1,2-cyclohexandiamine (abbreviated as dach), there are three stereo-isomers according to the following steric structures of the 1,2-cyclohexandiamine, namely 1,2-diaminocyclohexane moiety.

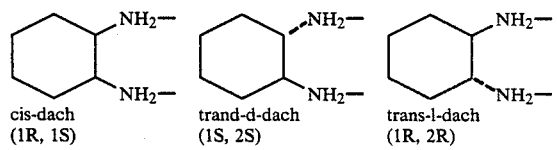

cis-dach (1R, 1S)   trand-d-dach (1S, 2S)   trans-l-dach (1R, 2R)

With the platinum(II)-steroid complex of the formula (I) according to this invention where the moiety

is the 2-(aminomethyl)cyclohexylamine (abbreviated as amcha), there are four stereo-isomers according to the following steric structures of the 2-(aminomethyl)cyclohexylamine, namely 1-amino-2-aminomethylcyclohexane moiety:

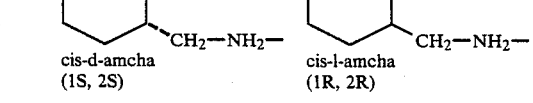

cis-d-amcha (1S, 2S)   cis-l-amcha (1R, 2R)

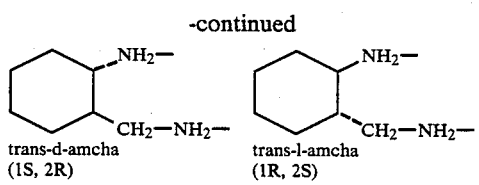

trans-d-amcha (1S, 2R)   trans-l-amcha (1R, 2S)

The platinum(II)-steroid complex of the formula (I) according to this invention, therefore, includes some different stereo-isomers as shown above, depending on the configuration of the 1,2-cyclohexanediamine or 2-(aminomethyl)cyclohexylamine which forms a ligand to the platinum atom.

In the platinum(II)-steroid complex of the formula (I), the steroid component may be selected from cortisone, hydrocortisone, prednisone, prednisolone, methylprednisone, methylprednisolone, 17-α-hydroprogesterone, estrone, estriol, progestrone, cholic acid, deoxycholic acid, androsterone, testosterone, testosterone propionate and the like.

In order to prepare the platinum(II)-steroid complex of the general formula (I) according to this invention, steroid hormone which becomes a leaving group is reacted with a nitrato ($NO_3$)-derivative or a nitrate of a platinum(II) complex compound where a desired carrier ligand compound is complexed with the platinum atom. Thus, the platinum(II)-steroid complex of the general formula (I) according to this invention may be prepared according to the process wherein such a dinitrato-platinum(II) complex, in which a desired particular ligand such as the 1,2-cyclohexanediamine (namely, dach) or the 2-(aminomethyl)cyclohexylamine (namely, amcha) ligand has coordinated the platinum(II) atom and which is represented by the formula:

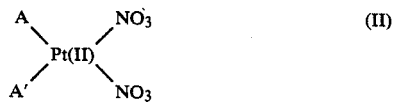

wherein A and A' are as defined above, is reacted with a steroid compound which will give the leaving group, with the reaction being conducted in a suitable solvent. The starting material, namely the dinitrato-platinum(II) complex of formula (II) may be prepared according to a known method, for example, the method disclosed in Japanese Patent Second Publication (KOKOKU) No. 29957/83 or U.S. Pat. Nos. 4,256,652; 4,255,347 and 4,551,524. Of the steroid compounds employed as the leaving groups, methylprednisolone is used as an antiemetic and is believed to exhibit synergistic effects as a carcinostatic agent.

The new platinum(II)-steroid complex of the formula (I) according to this invention exhibits anti-tumor activity against experimental tumors in mouse, such as L-1210, P-388 and S-180A (ascites tumor), and therefore is useful in chemotherapeutics of tumors. The new platinum(II)-steroid complex of this invention can be administered orally, intramuscularly or intraveneously. It can be formulated into capsules, powders, pellets, injections or micelle.

Suitable dosage of the platinum(II)-steroid complex of this invention is about 1 to 400 mg/kg/day.

The preparation of the novel platinum(II)steroid complex of the formula (I) according to this invention is now illustrated with reference to the following Examples. The data of elemental analysis and yield of the platinum(II)-steroid complex as prepared in these Examples are tabulated in Table 1 hereinafter. Compound Nos. given in Table 1 are corresponding to the Example Nos. in which the platinum(II) complex indicated was prepared.

EXAMPLE 1

Preparation of cortisone-(trans-l-dach)platinum(II) complex dinitrate of the formula:

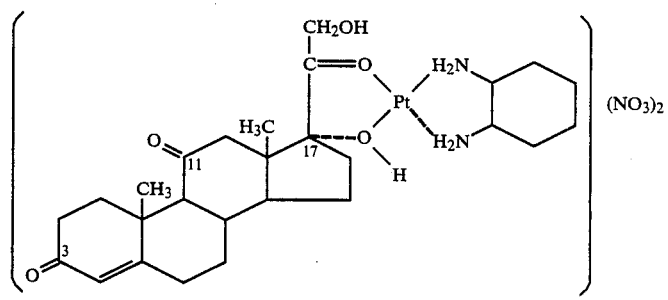

(1) Di-nitrato(trans-l-dach)platinum(II) complex, namely $(NO_3)_2$(trans-l-dach)platinum(II) complex (0.500 g, 1.154 mmol) represented by the formula:

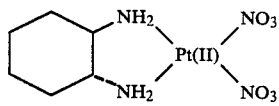

was dissolved in water (30 ml) under heating, to give an aqueous solution. Cortisone (0.416 g, 1.154 mmol) was also dissolved in hot ethanol (40 ml). After cooling both the resulting solutions, the ethanol solution of cortisone was added gradually in portions of about 2 ml to the aqueous solution of the $(NO_3)_2$(trans-l-dach)platinum-(II) complex as prepared, while stirring the latter solution in a flask on a magnetic stirrer. The resultant mixed solution turned to a yellow color. After completion of the addition of the cortisone solution, the mouth of the flask was covered with paraffin paper, the flask was shielded from light by covering with an aluminum foil, and the reaction mixture was stirred for 1-3 days for the reaction.

After the reaction, the reaction mixture was filtered to remove the insoluble matters therefrom, and the filtrate was concentrated to dryness in flash evaporator. 50% Aqueous ethanol (50 ml) was added to the residue as obtained, and the resulting mixture was stirred for 1 hour on a magnetic stirrer so as to dissolve the residue.

The resulting solution was filtered and the filtrate was concentrated to dryness. Pale yellow powder (711 mg) was obtained as the titled platinum(II) complex.

(2) Dinitrato(trans-l-dach)platinum(II) complex (0.43 g, 1 mmol) was dissolved in water (30 ml) under heating. To the thus-obtained aqueous solution, a solution which had been obtained by dissolving cortisone (0.360 g, 1 mmol) in ethanol (30 ml) under mild heating was gradually added in portions of 1–2 ml on a water bath (at about 50° C.), whereby the resulting mixture turned to a yellow color. The mixture was thereafter heated for about 2 hours on the water bath for the reaction. After allowing the reaction mixture to stand for one day, it was filtered and the filtrate was concentrated to dryness in a flash evaporator.

The residue was dissolved in 50% aqueous ethanol. After filtration of the solution so obtained, the filtrate was concentrated to dryness so that pale yellow powder was obtained as the titled platinum(II) complex.

EXAMPLE 2

Preparation of hydrocortisone-(trans-l-dach) platinum(II) complex dinitrate.

(1) $(NO_3)_2$(trans-l-dach)platinum(II) complex (0.500 g. 1.153 mmol) was dissolved in water (40 ml) under heating.

Hydrocortisone (0.418 g, 1.154 mmol) was also dissolved in hot ethanol (40 ml). After cooling both the resulting solutions, the ethanolic solution of hydrocortisone was added gradually in portions of about 2 ml to the aqueous solution of the $(NO_3)_2$(trans-l-dach) platinum(II) complex, while stirring the latter solution in a flask on a magnetic stirrer. The resultant mixed solution showed a yellow color. After completion of the addition, the mouth of the flask was covered with paraffin paper, the flask was shielded from light by covering with an aluminum foil, and the reaction mixture was stirred for 3 days for the reaction.

After the reaction, the reaction mixture was filtered to remove the insoluble matters therefrom, and the filtrate was concentrated to dryness in a flash evaporator. 50% Aqueous ethanol (50 ml) was added to the residue obtained, and the resulting mixture was stirred for about 1 hour on a magnetic stirrer so as to dissolve the residue. The resulting solution was filtered and the filtrate was then concentrated to dryness, thereby obtaining pale yellow powder (775 mg) as the titled platinum(II) complex.

(2) In this procedure, activated carbon was added as a catalyst. Activated carbon (0.200 g) was added to an aqueous solution of $(NO_3)_2$(trans-l-dach) platinum(II) complex, which had been prepared by dissolving $(NO_3)_2$ (trans-l-dach)platinum(II) complex (0.43 g, 1 mmol) in water (40 ml) under heating, while stirring said aqueous solution in a flask on a magnetic stirrer. To said aqueous solution was then added an ethanolic solution of hydrocortisone which had been prepared by dissolving hydrocortisone (0.418 g, 1.154 mmol) in hot ethanol (40 ml). The mouth of the flask containing the resulting mixture was covered with paraffin paper, the flask was shielded from light by covering with an aluminum foil, and the mixture in the flask was filtered and the filtrate was concentrated to dryness in a flash evaporator.

An yellowish crystalline substance so obtained was dissolved in 50% aqueous methanol 10 ml). After filtration of the resulting solution, the filtrate was concentrated to dryness by evaporation to give the titled platinum(II) complex substance (0.200 g).

(3) Dinitrato(trans-l-dach)platinum(II) complex 0.437 g, 1 mmol was dissolved in water (30 ml) under heating. Hydrocortisone (0.33 g, 1 mmol) was dissolved in hot ethanol (30 ml). While heating the aqueous solution of the $(NO_3)_2$ (trans-l-dach)platinum(II) complex on a water bath (at about 50° C.), the ethanolic solution of hydrocortisone was added thereto in portions of about 2 ml. The resultant mixed solution turned to a yellow color. After the addition, the resulting mixture was heated for about 2 hours on a water bath for the reaction. After the reaction mixture was allowed to stand for one day, it was filtered and the filtrate was concentrated to dryness.

The residue obtained was dissolved in 50% aqueous ethanol under stirring. After filtration of the solution, the filtrate was concentrated to dryness to afford the titled platinum(II) complex.

EXAMPLE 3

Preparation of cortisone-$(NH_3)_2$platinum(II) complex dinitrate $(NO_3)_2(NH_3)_2$-platinum(II) complex (0.353 g, 1 mmol) of the formula:

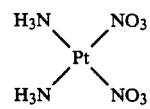

was dissolved in water (30 ml) under heating. Cortisone (0.360 g, 1 mmol) was also dissolved in hot ethanol 30 ml). The ethanolic solution of cortisone was added in portions of about 2 ml to the aqueous solution of the $(NO_3)_2(NH_3)_2$Pt(II) on a water bath, and the resultant mixture had a yellow color.

The mixture was heated at 50° C. for about 1 hour on a water bath.

After the reaction, the reaction mixture was filtered and the filtrate was concentrated to dryness. Subsequent to the dissolution of the resulting residue in 50% aqueous ethanol, the solution obtained was filtered and the filtrate was concentrated by evaporation, to yield the titled platinum(II) complex substance as pale yellow powder.

EXAMPLE 4

Preparation of cortisone-(ethylenediamine) platinum-(II) complex dinitrate $(NO_3)_2$ (ethylenediamine)platinum(II) complex (0.379 g, 1 mmol) of the formula

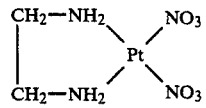

was dissolved in water (30 ml) under heating.

Cortisone (0.360 g, 1 mmol) was also dissolved in hot ethanol (30 ml). The cortisone solution was added in portions of about 2 ml to the aqueous solution of $(NO_3)_2$ (ethylenediamine)platinum(II) complex over a water bath. When heating was continued (at about 50° C.) over the water bath, the reaction mixture developed yellow color. After allowing the reaction mixture to stand for 1 hour, it was filtered, and the filtrate was concentrated to dryness. With agitation on a magnetic stirrer, the residue was dissolved in 50% aqueous ethanol. After filtration of the resulting solution, the filtrate was concentrated to dryness, thereby obtaining the titled product as pale yellow powder.

EXAMPLE 5

Preparation of hydrocortisone-(NH$_3$platinum(II) complex dinitrate (NO$_3$)$_2$(NH$_3$)$_2$platinum(II) complex (0.353 g, 1 mmol) was dissolved in water (30 ml) under heating. Hydrocortisone (0.362 g, 1 mmol) was also dissolved in hot ethanol (30 ml).

While heating the aqueous solution of (NO$_3$)$_2$(NH$_3$)$_2$platinum(II) (at about 50° C.) over a water bath, the ethanolic solution of hydrocortisone was added in portions of about 2 ml thereto. The color of the resulting aqueous mixture turned gradually to a yellow color.

The resultant mixture was heated for 1 hour on a water bath and was then filtered. The filtrate was concentrated to dryness in a flash evaporator. After dissolving the resultant residue in 50% aqueous ethanol on a magnetic stirrer, the solution obtained was filtered and the filtrate was concentrated to give pale yellow powder as the titled product.

EXAMPLE 6

Preparation of hydrocortisone-(ethylenediamine)platinum(II) complex dinitrate (NO$_3$)$_2$(ethylenediamine)platinum(II) complex (0.379 g, 1 mmol was dissolved in water (30 ml) under heating. Hydrocortisone (0.362 g, 1 mmol) was also dissolved in hot ethanol (30 ml).

While heating the aqueous solution of (NO$_3$)$_2$(ethylenediamine) platinum(II) complex (at about 50° C.) on a water bath, the ethanolic solution of hydrocortisone was added in portions of about 2 ml thereto. The resulting mixture solution showed a yellow color. After the mixture was heated further on the water bath for about 1 hour for the reaction, the reaction mixture was left over. After filtration of the reaction mixture, the filtrate was evaporated to dryness in a flash evaporator. The residue obtained was dissolved in 50% aqueous ethanol on a magnetic stirrer, followed by filtration. The filtrate was concentrated to dryness, thereby to afford pale yellow powder as the titled product.

EXAMPLE 7

Preparation of cortisone-(cis-dl-amcha)platinum(II) complex dinitrate (NO$_3$)$_2$(cis-dl-amcha)platinum(II) complex (0.447 g, 1 mmol) of the formula:

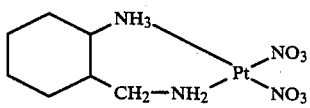

was dissolved in water (30 ml) under heating. Cortisone (0.360 g, 1 mmol) was also dissolved in hot ethanol (30 ml), and the resulting ethanolic solution was then added in small portions to the aqueous solution of (NO$_3$)$_2$(cis-dl-amcha)platinum(II) complex. The resultant mixture had a yellow color. The mixture was filtered, the filtrate was concentrated to dryness and the residue obtained was dissolved in 50% aqueous ethanol. After filtration of the resulting solution, the filtrate was concentrated to dryness by evaporation of the solvents, to obtain the titled product as pale yellow powder.

EXAMPLE 8

Preparation of cortisone-(trans-dl-amcha)platinum(II) complex dinitrate

The above titled substance was obtained by repeating the procedure of Example 7 except that (NO$_3$)$_2$(trans-dl-amcha)platinum(II) complex (0.447 g, 1 mmol) was employed in lieu of the (NO$_3$)$_2$ (cis-dl-amcha)platinum(II) complex.

EXAMPLE 9

Preparation of hydrocortisone-(cis-dl-amcha)-platinum(II) complex dinitrate

The above titled substance was obtained by repeating the procedure of Example 8 except that hydrocortisone (0.362 g, 1 mmol) was employed in place of cortisone.

EXAMPLE 10

Preparation of hydrocortisone-(trans-dl-amcha)-platinum(II) complex dinitrate

The above titled substance was obtained by repeating the procedure of Example 9 except for the use of (NO$_3$)$_2$(trans-dl-amcha)platinum(II) (0.447 g, 1 mmol) in lieu of (NO$_3$)$_2$ (cis-dl-amcha)platinum(II).

EXAMPLE 11

Preparation of prednisolone-(trans-l-dach) platinum(II) complex dinitrate (NO$_3$)$_2$(trans-l-dach)platinum(II) (0.433 g, 1 mmol) was dissolved in water (30 ml) under heating. Prednisolone (0.360 g, 1 mmol) was also dissolved in hot ethanol (30 ml) and the resulting ethanolic solution was then added in portions of about 2 ml to the aqueous solution of (NO$_3$)$_2$-(trans-l-dach)platinum(II) complex while heating the latter solution over a water bath (at about 50° C.). The resultant solution mixture turned to a yellow color. This mixture was heated (at about 50° C.) for about 1 hour over the water bath and was then filtered. The filtrate was thereafter concentrated to dryness by evaporation of the solvents, in a flash evaporator. The residue as obtained was taken up in 50% aqueous ethanol on a magnetic stirrer. After filtration of the resulting solution, the filtrate was concentrated to dryness, to give the titled platinum(II) complex as pale yellow powder.

EXAMPLE 12

Preparation of prednisolone-(trans-l-dach)platinum(II) complex dinitrate

EXAMPLE 13

Preparation of methylprednisolone-(trans-l-dach)-platinum(II) complex dinitrate

EXAMPLE 14

Preparation of methylprednisolone propionate-(trans-l-dach)platinum(II) complex dinitrate The above titled substances were prepared separately by repeating the procedure of Example 11 except that prednisolone (0.358 g, 1 mmol) (Example 12), methylprednisolone (0.358 g, 1 mmol) (Example 13) and methylprednisolone propionate (0.374 g, 1 mmol) (Example 14) were used respectively in place of the prednisolone.

EXAMPLE 15

Preparation of prednisolone-(cis-dl-amcha)platinum-(II) complex dinitrate (NO$_3$)$_2$(cis-dl-amcha)platinum(II) complex (0.447 g, 1 mmol) was dissolved in water (30 ml) under heating. Prednisolone (0.358 g, 1 mmol) was also dissolved in the ethanol (30 ml) on a water bath and the resulting ethanolic solution was then added in small portions to the aqueous solution of (NO$_3$)$_2$(cis-dl-amcha)platinum(II) complex. The resultant mixture turned to a yellow color. The mixture was filtered and the filtrate was concentrated to dryness. The residue as obtained was dissolved in 50% aqueous ethanol on a magnetic stirrer. After filtration of the resulting solution, the filtrate was concentrated to dryness to afford the above titled complex as a pale yellow powder.

EXAMPLE 16

Preparation of prednisone-(trans-dl-amcha)platinum-(II) complex dinitrate

The above titled substance was prepared by repeating the procedure of Example 15 except that (NO$_3$)$_2$(trans-dl-amcha)platinum(II) complex (0.447 g, 1 mmol) was employed in lieu of the (NO$_3$)$_2$(cis-dl-amcha)platinum-(II).

EXAMPLE 17

Preparation of the prednisolone-(cis-dl-amcha)-platinum(II) complex dinitrate

The above titled substance was obtained by following the procedure of Example 15 except that prednisolone was used instead of prednisone.

EXAMPLE 18

Preparation of prednisolone-(trans-dl-amcha)-platinum(II) complex dinitrate

The above titled substance was obtained by following the procedure of Example 17 except for the use of (NO$_3$)$_2$(trans-dl-amcha)platinum(II) complex (0.447 g, 1 mmol) in lieu of (NO$_3$)$_2$(cis-dl-amcha)platinum(II).

EXAMPLE 19

Preparation of methylprednisolone-(cis-dl-amcha)-platinum(II) complex dinitrate

The above titled substance was obtained by following the procedure of Example 15 except for the use of methylprednisolone instead of prednisone.

EXAMPLE 20

Preparation of methylprednisolone-(trans-dl-amcha)-platinum(II) complex dinitrate The above titled substance was obtained by repeating the procedure of Example 20 except that (NO$_3$)$_2$(trans-dl-amcha)platinum(II) (0.447 g, 1 mmol) was used in lieu of (NO$_3$)$_2$(cis-dl-amcha)platinum(II) complex.

EXAMPLE 21

Preparation of 17-α-hydroxyprogesterone-(trans-l-dach)platinum(II) complex dinitrate (NO$_3$)$_2$(trans-l-dach)platinum(II) complex (0.433 g 1 mmol) was dissolved in water (30 ml) under heating. 17-α-hydroprogesterone (0.330 g, 1 mmol) was also dissolved in hot ethanol (30 ml) and the resulting ethanolic solution was then added in portions of about 2 ml to the aqueous solution of (NO$_3$)$_2$(trans-l-dach)-platinum(II) complex. After filtration of the resulting mixture, the filtrate was concentrated to dryness and the residue obtained was dissolved in 50% aqueous ethanol on a magnetic stirrer. Subsequent to filtration of the resultant solution, the filtrate was concentrated to dryness so that the above titled substance was obtained.

EXAMPLE 22

Preparation of 17-α-hydroprogesterone-(cis-dl-amcha)platinum(II) complex dinitrate The above titled substance was obtained by following the procedure of Example 21 except for the use of (NO$_3$)$_2$(cis-dl-amcha)platinum(II) complex (0.447 g, 1 mmol) in lieu of (NO$_3$)$_2$(trans-l-dach)platinum(II) complex.

EXAMPLE 23

Preparation of 17-α-hydroxyprogesterone-(trans-dl-amcha)platinum(II) complex dinitrate The above titled substance was obtained by following the procedure of Example 21 except for the use of (NO$_3$)$_2$-(trans-dl-amcha)platinum(II) complex (0.447 g, 1 mmol) in lieu of (NO$_3$)$_2$(trans-l-dach)platinum(II) complex.

EXAMPLE 24

Preparation of progesterone-(trans-l-dach)platinum-(II) complex dinitrate

The above titled substance was obtained by following the procedure of Example 21 except for the use of progesterone (0.314 g, 1 mmol) instead of 17-α-hydroxyprogesterone.

EXAMPLE 25

Preparation of progesterone-(cis-dl-amcha)platinum-(II) complex dinitrate

The titled substance was obtained by following the procedure of Example 24 except that (NO$_3$)$_2$(cis-dl-amcha)platinum(II) complex (0.447 g, 1 mmol) was used in lieu of (NO$_3$)$_2$(trans-l-dach)platinum(II) complex.

EXAMPLE 26

Preparation of progesterone-(trans-dl-amcha)-platinum(II) complex dinitrate

The titled substance was obtained by following the procedure of Example 24 except for the use of (NO$_3$)$_2$(-trans-dl-amcha)platinum(II) complex (0.447 g, 1 mmol) in lieu of (NO$_3$)$_2$(trans-l-dach)platinum(II) complex.

EXAMPLE 27

Preparation of estriol-(trans-l-dach)platinum(II) complex dinitrate

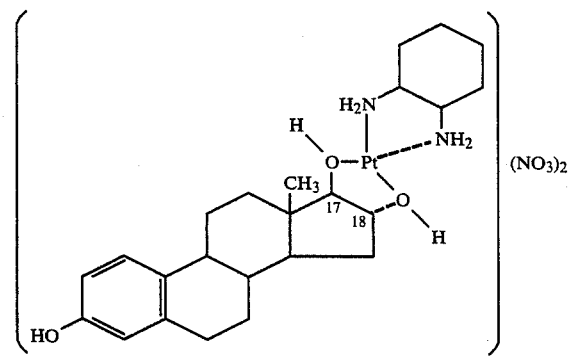

EXAMPLE 28

Preparation of estrone-(trans-l-dach)platinum(II) complex dinitrate

The titled substances were prepared separately by repeating the procedure of Example 21 except that estriol (0.288 g, 1 mmol)(Example 27) and estrone (0.270 g, 1 mmol) (Example 28) were used respectively in place of the 17-α-hydroxyprogesterone.

EXAMPLE 29

Preparation of cholic acid-(trans-l-dach)platinum(II) complex dinitrate $(NO_3)_2$(trans-l-dach)platinum(II) complex (0.431 g, 1 mmol was dissolved in water (30 ml) under heating. Cholic acid (0.324 g, 1 mmol) was also dissolved in hot ethanol (30 ml). Both the resulting solutions were combined together and the resulting mixture was then heated (at 50°–60° C.) on a water bath for the reaction. After filtration of the reaction mixture, the filtrate was concentrated to dryness in a flash evaporator so that the titled substance was obtained.

EXAMPLE 30

Preparation of (cholic acid)$_2$(trans-l-dach)platinum-(II) complex $(NO_3)_2$(trans-l-dach)platinum(II) complex (0.431 g, 1 mmol) was dissolved in water (30 ml) under heating. Cholic acid (0.648 g, 2 mmol) was also dissolved in hot ethanol (30 ml). When both the resulting solutions were combined together, the resultant mixture solution was first a clear solution. When this mixture solution was then heated (at 50°–60° C.) over a water bath, a precipitate was formed several minutes later. The precipitate was collected by filtration and then washed with water and then with ethanol to give in titled platinum(II) complex substance.

EXAMPLE 31

Preparation of (deoxycholic acid)(trans-l-dach)-platinum(II) complex

The above titled substances was obtained by repeating the procedure of Example 30 except that sodium deoxycholate (0.828 g, 2 mmol) was used instead of the cholic acid.

EXAMPLE 32

Preparation of Androsterone-(trans-l-dach)platinum-(II) complex dinitrate

The above titled substance was obtained at a yield of 60% by repeating the procedure of Example 11 above, except that androsterone (0.29 g, 1 mmol) was used in place of the prednisolone.

EXAMPLE 33

Preparation of testosterone-(trans-l-dach)platinum-(II) complex dinitrate

The above titled substance was obtained at yield of 60% by repeating the procedure of Example 11 above, except that testosterone (0.288 g, 1 mmol) was used in place of the prednisolone.

EXAMPLE 34

Preparation of testosterone proprionate-(trans-l-dach)platinum(II) dinitrate

The above titled substance was obtained at a yield of 60% by repeating the procedure of Example 11 except that testosterone propionate (0.433 g, 1 mmol) was used in place of prednisolone.

The elemental analysis values and yields of the platinum-steroid complexes as prepared in the above Examples 1–34 are summarized in the following Table 1.

TABLE 1

| Example No. | Calculated value (%) | | | Found value (%) | | | Yield (%) |
|---|---|---|---|---|---|---|---|
| | H | C | N | H | C | N | |
| 1-(1) | 5.33 | 40.86 | 7.06 | 5.50 | 40.95 | 6.96 | 77.6 |
| 1-(2) | 5.33 | 40.86 | 7.06 | 5.05 | 40.96 | 7.07 | 80 |
| 2-(1) | 5.57 | 40.75 | 7.04 | 5.85 | 41.26 | 6.73 | 84.4 |
| 2-(2) | 5.91 | 44.26 | 5.73 | 6.15 | 44.90 | 5.70 | 25 |
| 2-(3) | 5.57 | 40.75 | 7.04 | 5.41 | 40.80 | 7.05 | 85 |
| 3 | 4.50 | 35.44 | 11.81 | 4.90 | 34.63 | 11.31 | 80 |
| 4 | 4.87 | 37.34 | 11.36 | 4.30 | 36.92 | 11.26 | 90 |
| 5 | 4.76 | 35.76 | 11.78 | 4.70 | 35.62 | 10.86 | 85 |
| 6 | 5.12 | 37.24 | 11.33 | 5.29 | 37.44 | 11.40 | 90 |
| 7 | 6.19 | 41.63 | 6.93 | 6.08 | 41.50 | 7.03 | 80 |
| 8 | 6.19 | 41.63 | 6.93 | 5.30 | 38.87 | 7.43 | 80 |
| 9 | 6.42 | 41.53 | 6.92 | 6.40 | 41.43 | 7.01 | 80 |
| 10 | 6.42 | 41.53 | 6.92 | 5.51 | 38.35 | 7.49 | 85 |
| 11 | 5.05 | 40.96 | 7.07 | 5.69 | 41.54 | 7.26 | 88 |
| 12 | 5.05 | 40.96 | 7.07 | 5.49 | 40.16 | 7.12 | 90 |
| 13 | 5.56 | 42.47 | 7.07 | 5.03 | 41.78 | 7.98 | 85 |
| 14 | 5.66 | 43.91 | 6.07 | 5.18 | 43.59 | 7.36 | 80 |
| 15 | 5.96 | 41.73 | 6.95 | 6.05 | 41.58 | 7.02 | 80 |
| 16 | 5.96 | 41.73 | 6.95 | 5.37 | 42.26 | 6.59 | 80 |
| 17 | 6.19 | 41.63 | 6.93 | 6.25 | 41.60 | 6.98 | 80 |
| 18 | 6.19 | 41.63 | 6.93 | 5.39 | 40.95 | 7.18 | 80 |
| 19 | 5.60 | 42.38 | 6.82 | 5.50 | 42.40 | 6.80 | 80 |
| 20 | 5.60 | 42.38 | 6.82 | 5.93 | 43.01 | 6.04 | 85 |
| 21 | 5.85 | 40.62 | 7.29 | 5.71 | 41.61 | 7.16 | 63 |
| 22 | 5.89 | 42.40 | 7.32 | 6.00 | 43.03 | 7.54 | 60 |
| 23 | 5.89 | 42.40 | 7.32 | 5.83 | 42.34 | 7.38 | 60 |
| 24 | 5.98 | 41.14 | 7.44 | 5.91 | 41.53 | 7.68 | 60 |
| 25 | 5.89 | 43.37 | 7.49 | 5.52 | 42.04 | 8.13 | 60 |
| 26 | 5.89 | 43.37 | 7.49 | 5.78 | 41.81 | 6.79 | 60 |
| 27 | 5.53 | 39.83 | 7.74 | 5.54 | 40.98 | 6.93 | 60 |
| 28 | 5.12 | 40.96 | 7.96 | 5.04 | 41.03 | 7.70 | 60 |
| 29 | 6.41 | 42.75 | 4.98 | 7.15 | 43.60 | 4.05 | 65 |
| 30 | 8.35 | 57.60 | 2.48 | 8.55 | 57.44 | 2.48 | 85 |
| 31 | 8.43 | 59.39 | 2.52 | 7.93 | 58.57 | 2.67 | 80 |
| 32 | 6.08 | 41.49 | 7.74 | 6.02 | 41.45 | 7.71 | 60 |
| 33 | 5.82 | 41.60 | 7.76 | 5.78 | 41.23 | 7.81 | 60 |
| 34 | 5.92 | 43.42 | 7.20 | 5.62 | 43.39 | 7.81 | 60 |

Experiment 1

Antitumor activity of the platinum(II)-steroid complex of this invention in mice against Leukemia L-1210 is now estimated.

To test the antitumor activity of the platinum(II)-steroid complexes according to this invention, $10^5$ cells/mouse of Leukemia L-1210 were transplanted by intraperitoneal injection to groups of $CDF_1$ mice (6 mice in each group) on day 0. On the next day after the transplantation and days 5 and 9 after the transplantation of Leukemia L-1210 cells, the platinum(II)-steroid complex under test was administered by intraperitoneal injection to the test mice. The antitumor activity of the test platinum(II)-steroid complex was evaluated by means of the ratio (%) of prolongation of mean survival days of the treated mice, in term of the values of T/C %, namely the value of 100 times the mean survival period of the groups of mice treated with the test platinum(II)-steroid complex, divided by the mean survival period of the comparative groups of mice which were not treated with the test platinum(II)-steroid complex. The test results are as shown in Table 2 below. In Table 2, the T/C (%) values of higher than 125% means that the tested platinum(II)-steroid complex has a substantial antitumor activity.

In Table 2, the numerical figure given in parenthesis denotes the number of the mice as entirely cured in each group of mice treated. The term "T" denotes that the incurred decrease in body weight of the treated mice within 5 days of the test exceeded the lowest limit value (−4 g) for judgement of the toxic effects of the test compound. The test results shown in Table 2 demonstrates that the platinum(II)steroid complexes of this invention have a significant antitumor activity.

dach)platinum(II) complex dinitrate, along with a curve (DS-2) which represents the arithmetic sum of an ultraviolet absorption spectrum of cortisone, plus an ultraviolet absorption spectrum of the starting $(NO_3)_2$(trans-l-dach)Pt(II) complex;

FIG. 10 shows a curve (C-3) which represents an ultraviolet absorption spectrum of progesterone-(trans-l-dach)platinum(II) complex dinitrate, along with a curve (DS-3) which represents the arithmetic sum of an

TABLE 2

| Tested Compound No. (Example No.) | Ratio (%) of prolongation of mean survival period (T/C, %) Dose (mg/kg) | | | | | | | | | | |
|---|---|---|---|---|---|---|---|---|---|---|---|
| | 400 | 200 | 100 | 50 | 25 | 12.5 | 6.25 | 3.12 | 1.56 | 0.78 | 0.39 |
| 1 | | | | 0 | 0 | 337(5) | 247 | 152 | 154 | | |
| 2 | | | | | 0 | 376(4) | 402(6) | 195 | 167 | 131 | 115 |
| 3 | | | | | 158 | 179 | | | | | |
| 4 | | | | | 143 | 125 | | | | | |
| 7 | | | | | | 262(1) | 260(1) | 142 | | | |
| 9 | | | | | | 240 | 234(1) | 173 | | | |
| 11 | | | | | 0 | 306(3) | 293(1) | | | | |
| 12 | | | | | T249(3) | 316(2) | 274(1) | | | | |
| 13 | | | | | 0 | 302(2) | 351(4) | | | | |
| 14 | | | | | 0 | 306(3) | 322(3) | | | | |
| 15 | | | | | 262(2) | 244(2) | 191 | | | | |
| 17 | | | | T110 | 268(2) | 335(4) | | | | | |
| 19 | | | | T 94 | 217(2) | 278(2) | | | | | |
| 21 | | | | 0 | T124 | 268(2) | 363(5) | 195 | 148 | | |
| 24 | | | | 0 | 0 | 362(5) | 345(4) | 234(1) | 137 | 128 | 113 |
| 27 | | | | 0 | 0 | 203(2) | | | | | |
| 28 | | | | | T113 | 280(2) | 219(1) | | | | |
| 29 | | | | 197 | 168 | 135 | | | | | |
| 30 | | | 103 | 111 | 101 | 101 | | | | | |
| 31 | | | 159 | 129 | 123 | | | | | | |
| Comparative compound* | | 100 | | | 100 | 100 | 100 | 100 | 100 | 100 | 100 |

*Comparative compound: $(NO_3)_2$-(trans-l-dach)platinum(II) complex

BRIEF DESCRIPTION OF THE DRAWINGS

With reference to the accompanying drawings.

Figure 11:
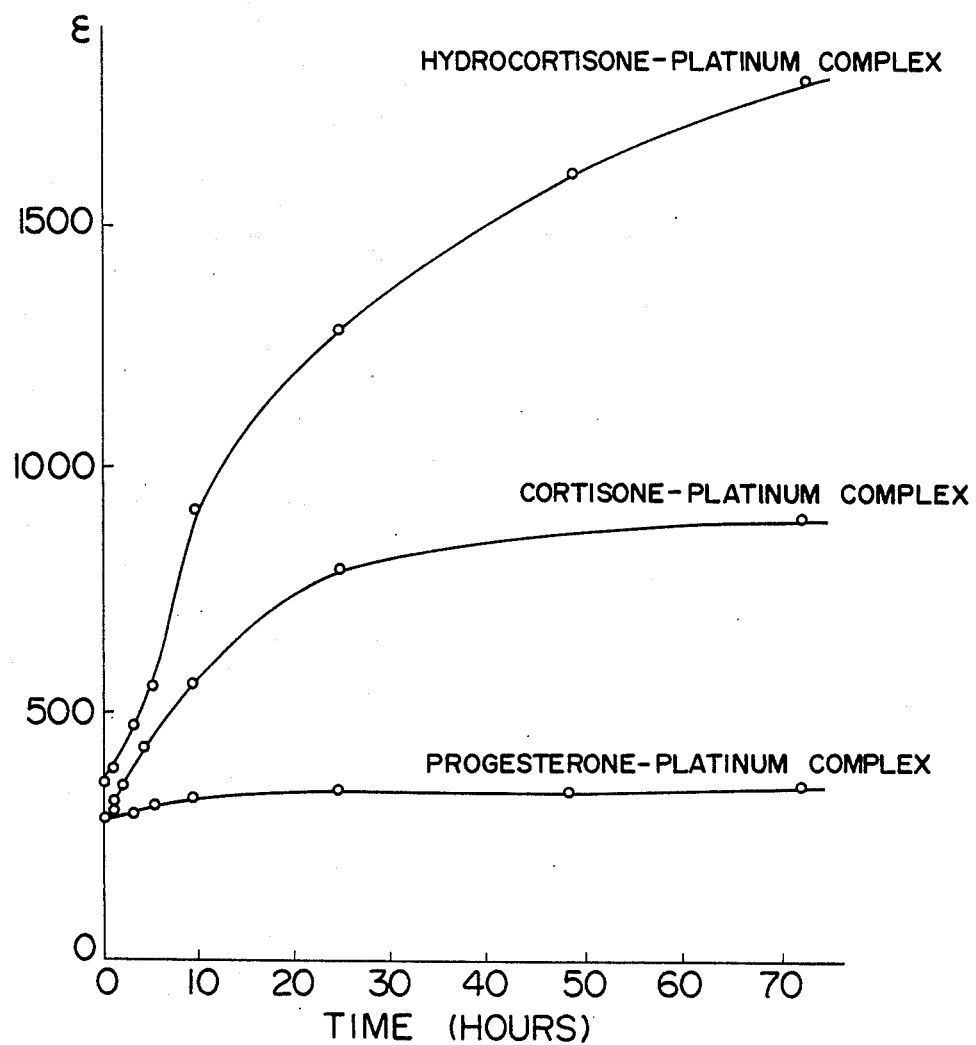
Figure 12:
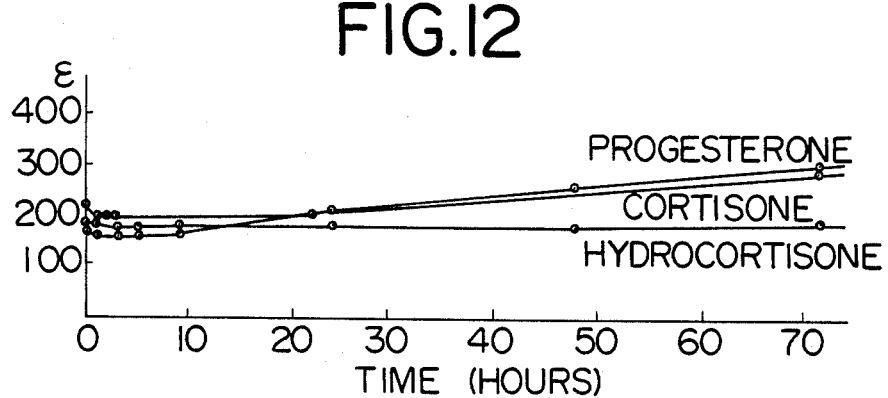
Figure 13:
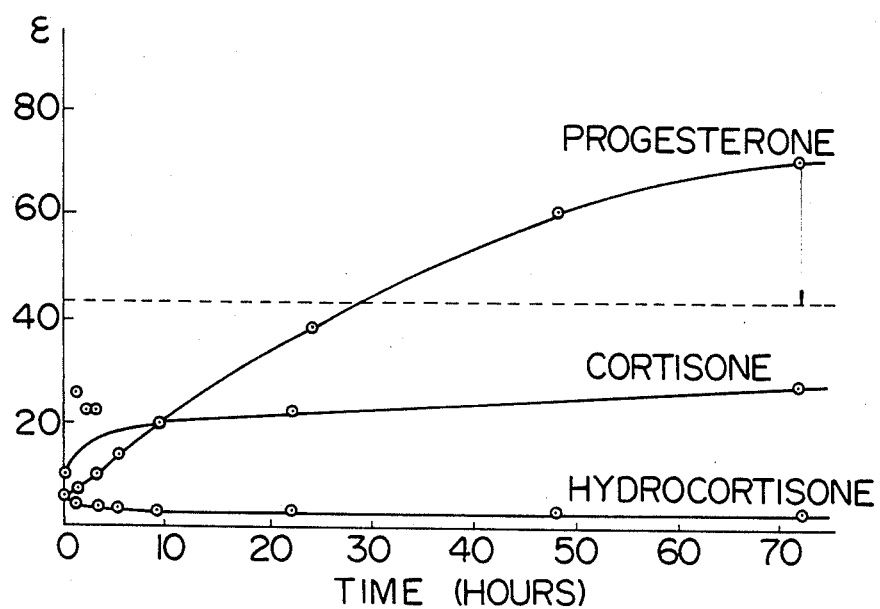

FIG. 11 shows curves which represent respectively the variations in the absorbance index ($\epsilon$) of the respective complexes of $(NO_3)_2$(trans-l-dach)platinum(II) with hydrocortisone, cortisone and progesterone, as measured at 290 nm and with the passage of time (hours) after the solutions of the starting materials were mixed together;

FIG. 12 shows curves which represent respectively the variations in the absorbance index ($\epsilon$) of progesterone, cortisone and hydrocortisone separately dissolved in aqueous alkaline solutions of sodium hydroxide, as measured at 290 nm and with the passage of time (hours) after a solution of each steroid compound was mixed with the aqueous sodium hydroxide solution;

FIG. 13 shows curves which represent respectively the variations in the absorbance index ($\epsilon$) of progesterone, cortisone and hydrocortisone separately dissolved in aqueous alkaline solutions of sodium hydroxide, as measured in the visible light wave length region, namely at 370 nm or at 420 nm, and with the passage of time (hours) after a solution of each steroid compound was mixed with the aqueous sodium hydroxide solution.

Further, infrared absorption spectra were measured separately on seven particular compounds amongst the platinum(II)-steroid complexes of this invention as obtained in the above Examples 1–34, and these IR spectrum curves are shown in FIGS. 1–7 of the accompanying drawings.

In addition, the following experiments were conducted in order to demonstrate that each platinum(II)-steroid complex as prepared according to this invention is not a mere physical mixture of its respective component compounds but a chemical complex compound.

Thus, the state of bonding between the steroid compound and platinum atom in each of some platinum-steroid complexes of this invention was investigated by measurement of its absorption spectrum in the ultraviolet and visible wave length region, and by determination of variations in pH of an aqueous solution containing the complex.

(A) Measurement of absorption spectra of the ultraviolet rays:

(a) Preparation of solutions of the starting materials:

Hydrocortisone, cortisone and progesterone were separately dissolved in three portions of ethanol. On the side, $(NO_3)_2$(trans-l-dach)platinum(II) complex (hereinafter merely called "starting platinum complex") was dissolved in water to provide its aqueous solution. In both cases, the steroid compound and the starting platinum complex were separately dissolved to a concentration of 0.02 mol/l in ethanol and in water, respectively.

(b) Measurement of absorption spectra of the ultraviolet region:

Each of the steroid solutions so prepared was mixed with the solution of the starting platinum complex prepared, at a volume ratio of 1:1. Just after the mixing, namely at the time of 0th hour after the mixing, the value of UV absorption of each of the mixed solutions was measured in a wavelength range of 500–340 nm in the case of the initially prepared solutions, in a wavelength range of 350–280 nm in the case of the tenfold diluted solutions and in a wavelength range of 300–190 nm in the case of the hundredfold diluted solutions, respectively.

After mixing the steroid solution with the starting platinum complex solution, UV absorption value of each platinum-steroid complex as formed in each mixed solution was similarly measured at the times of 1st, 3rd, 5th, 9th, 24th, 48th and 72nd hours after the mixing. 50% aqueous ethanol was used as a control.

In order to show that the UV absorption value so measured of the platinum-steroid complex was not the total sum of the individual UV absorptions of the starting materials (namely, the steroid compound and starting platinum complex), another tests were made. Thus, the starting materials were separately dissolved in 50% aqueous ethanol under stirring. UV absorption of the ethanolic solutions so prepared were measured at the 72th hour after the dissolution, in the same manner as in the case of the above measurement of the UV absorption of the steroid-platinum complex. A curve which represents each of the ultraviolet absorption spectra so measured was plotted in the following manner.

Wave lengths were indicated along the axis of abscissas, while the logarithms (log $\epsilon$) of the molar absorbance index ($\epsilon$) so evaluated were indicated along the axis of ordinates. The UV absorption of the platinum-complex solutions as measured at an elapsed time of 72 hours after the mixing of the solutions are plotted to draw the adsorption spectrum curves as shown by dotted lines (C-1, C-2, C-3) in FIGS. 8–10, respectively.

Figure 1:
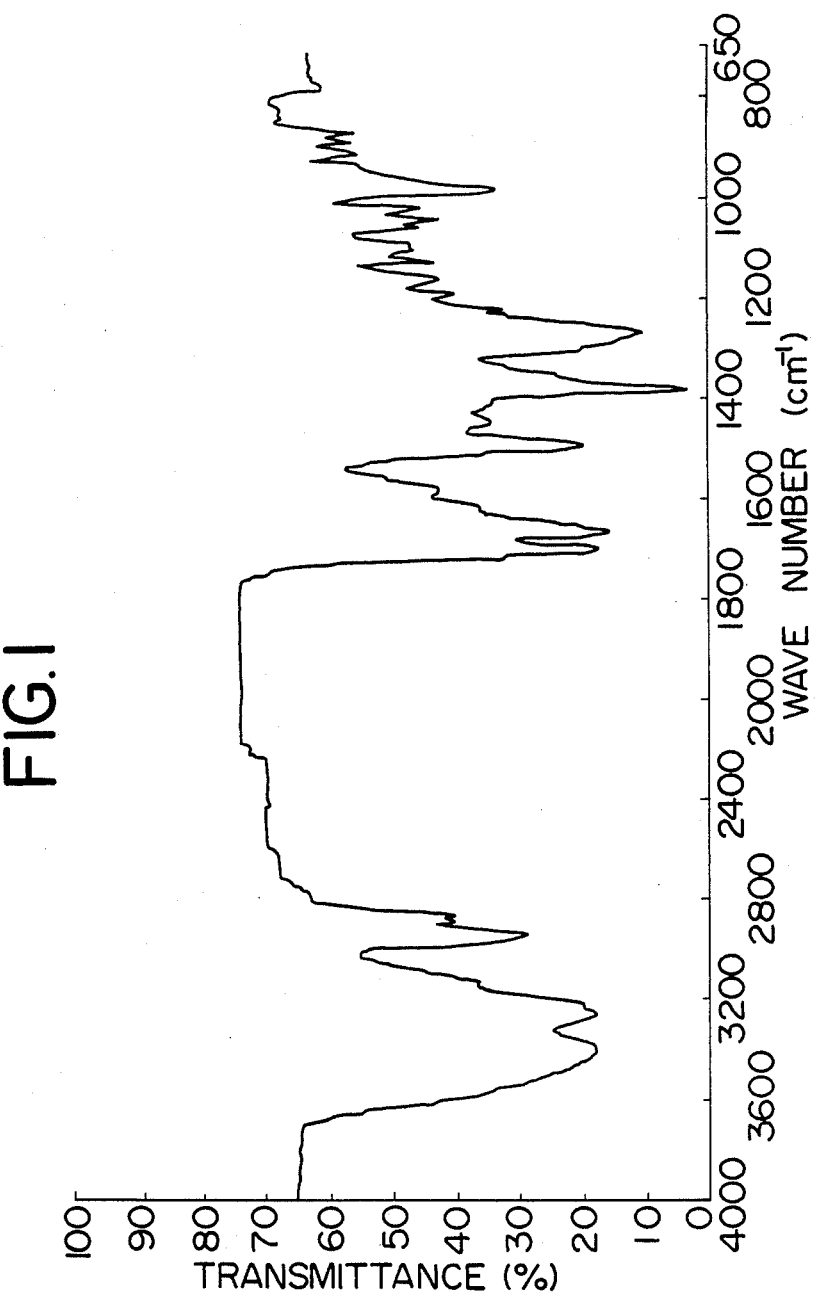
FIG. 1 shows a curve for an infrared absorption spectrum of cortisone(trans-l-dach)platinum(II) complex dinitrate.
Figure 2:
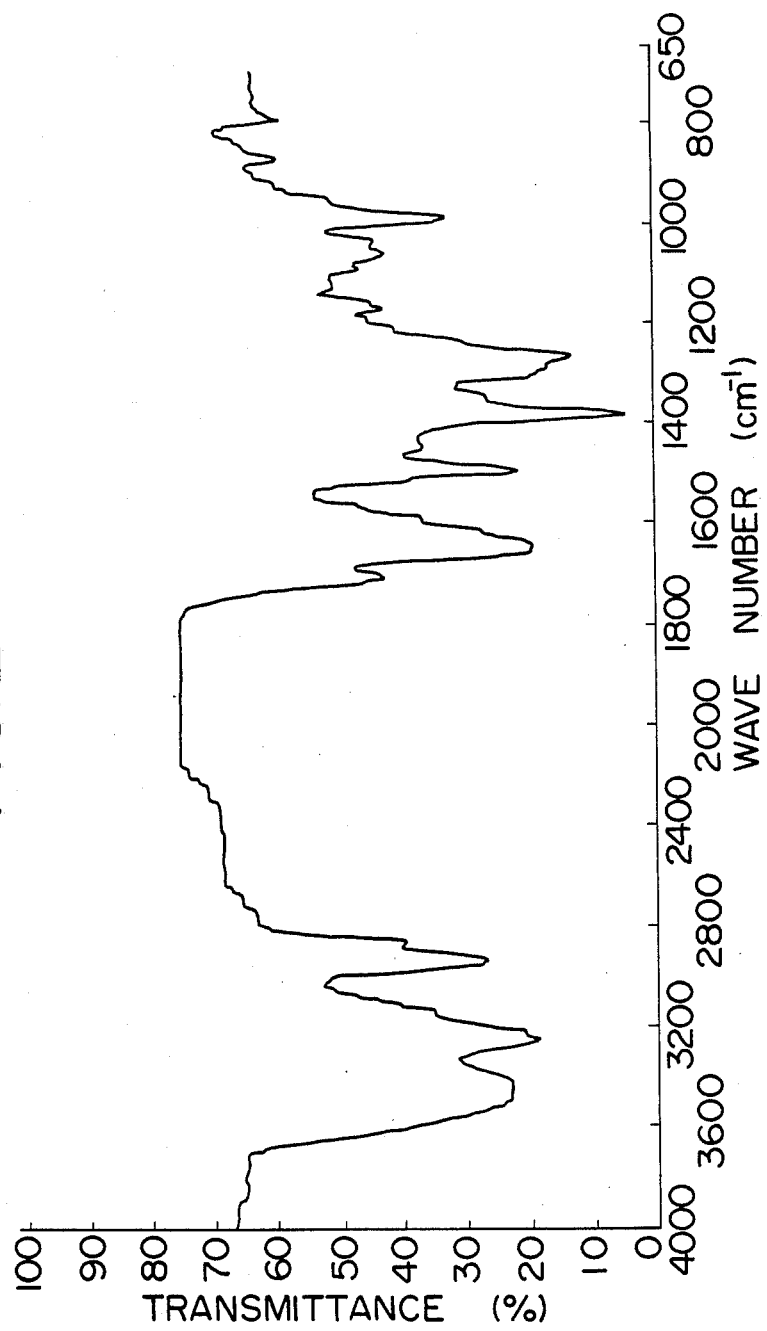
FIG. 2 shows a curve for an infrared absorption spectrum of hydrocortisone (trans-l-dach)platinum(II) complex dinitrate.
Figure 3:
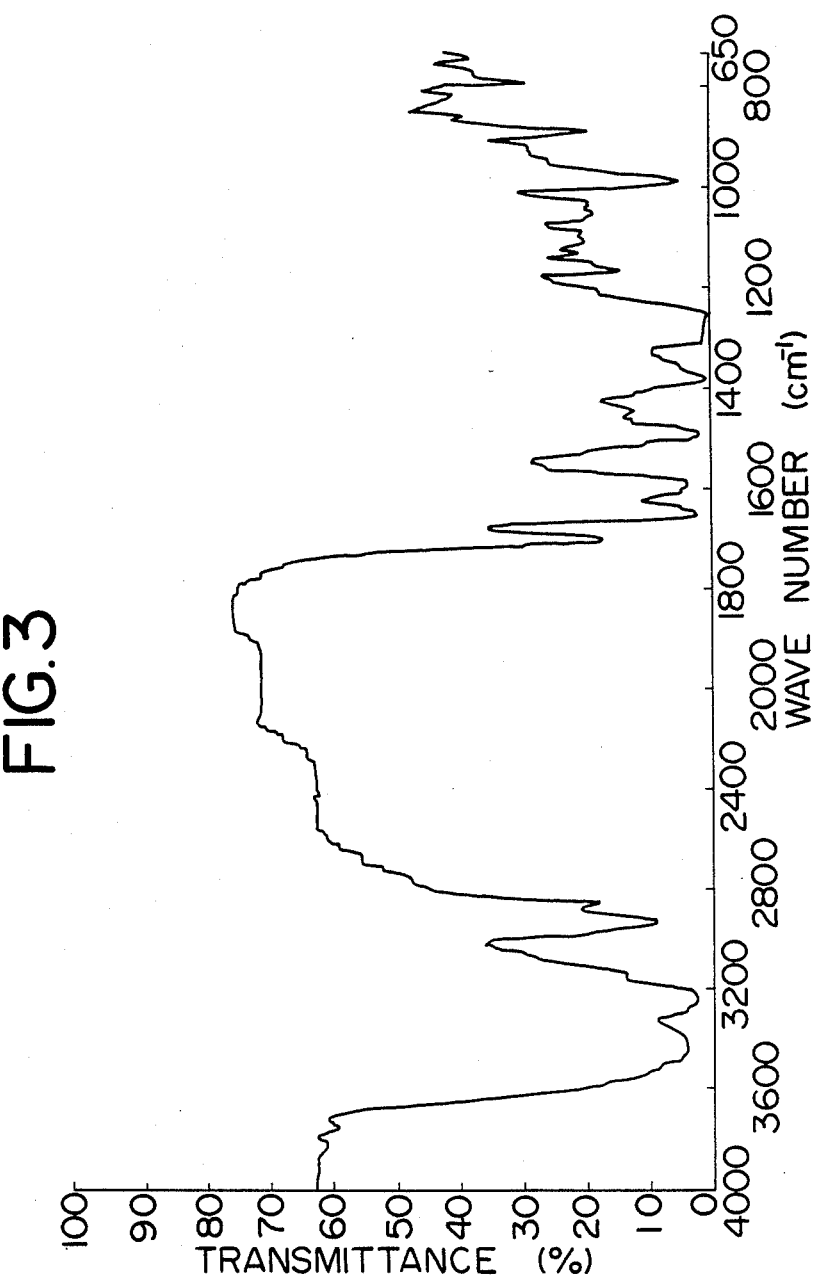
FIG. 3 shows a curve for an infrared absorption spectrum of prednisolone(trans-l-dach)platinum(II) complex dinitrate.
Figure 4:
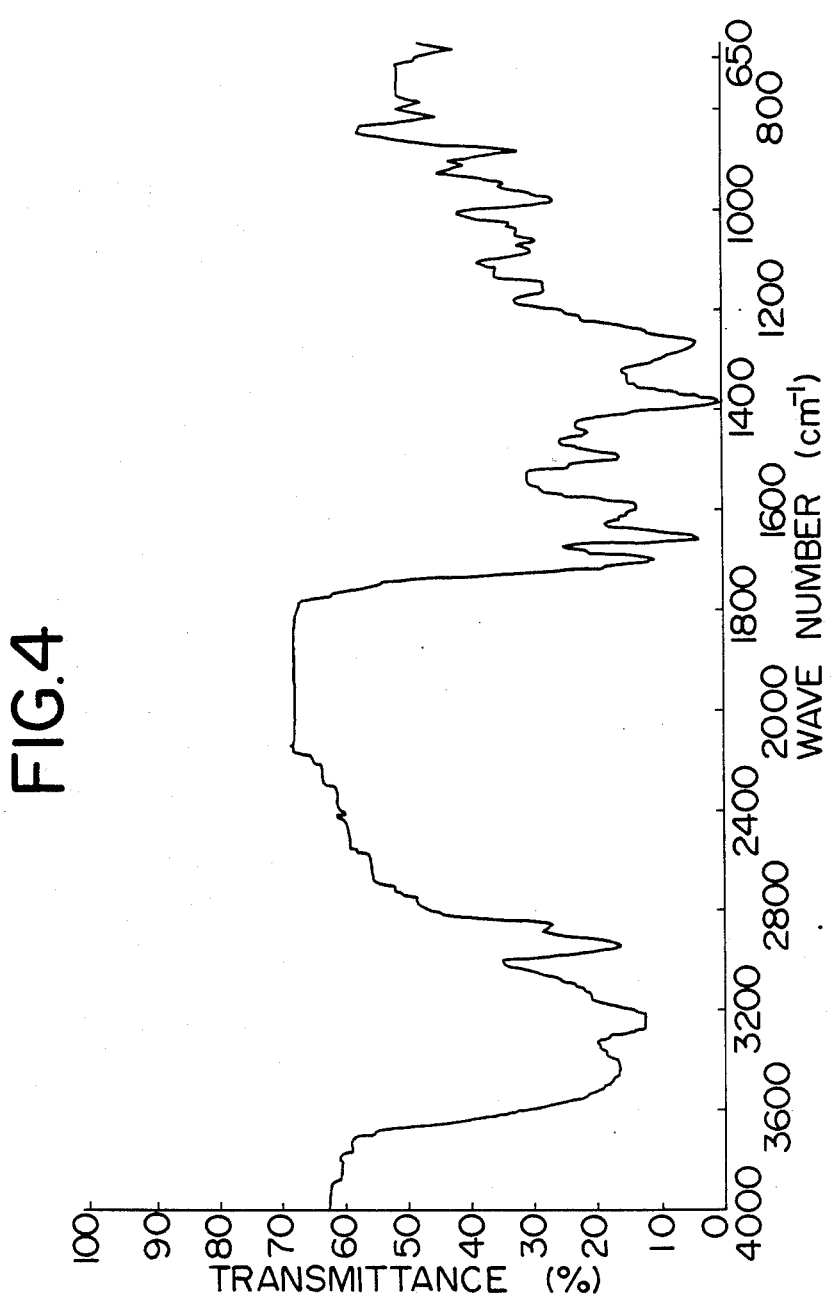
FIG. 4 shows a curve for an infrared absorption spectrum of prednisone(trans-l-dach)platinum(II) complex dinitrate.
Figure 5:
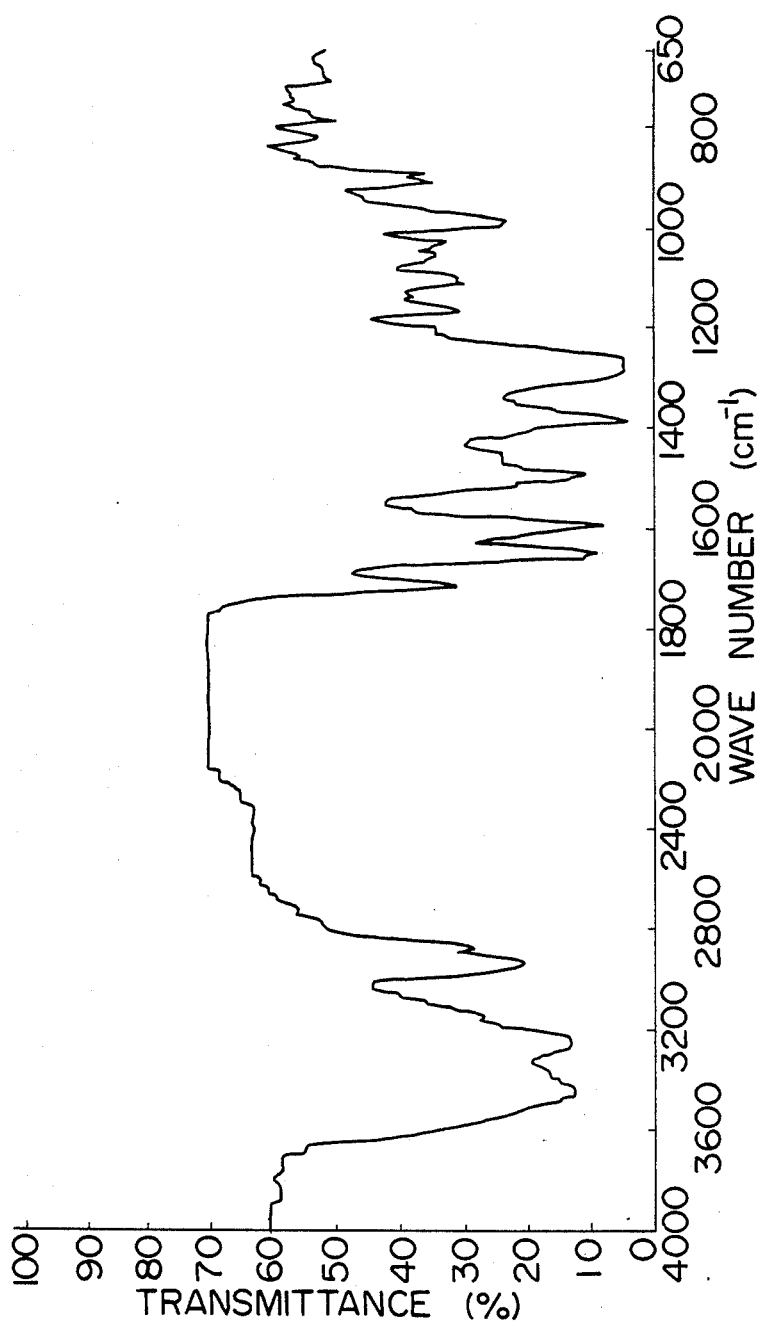
FIG. 5 shows a curve for an infrared absorption spectrum of methylprednisolone propionate(trans-l-dach)platinum(II) complex dinitrate.
Figure 6:
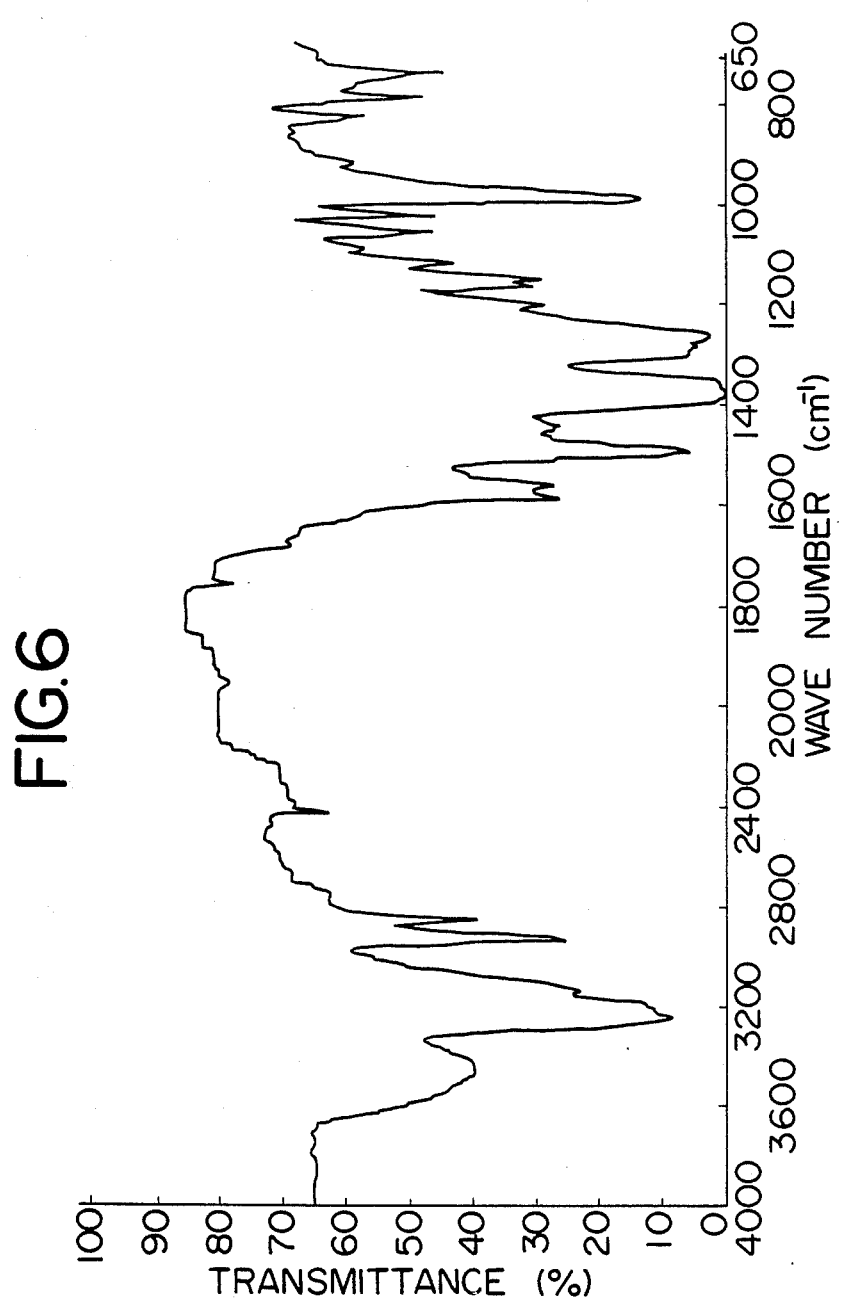
FIG. 6 shows a curve for an infrared absorption spectrum of progesterone(trans-l-dach)platinum(II) complex dinitrate.
Figure 7:
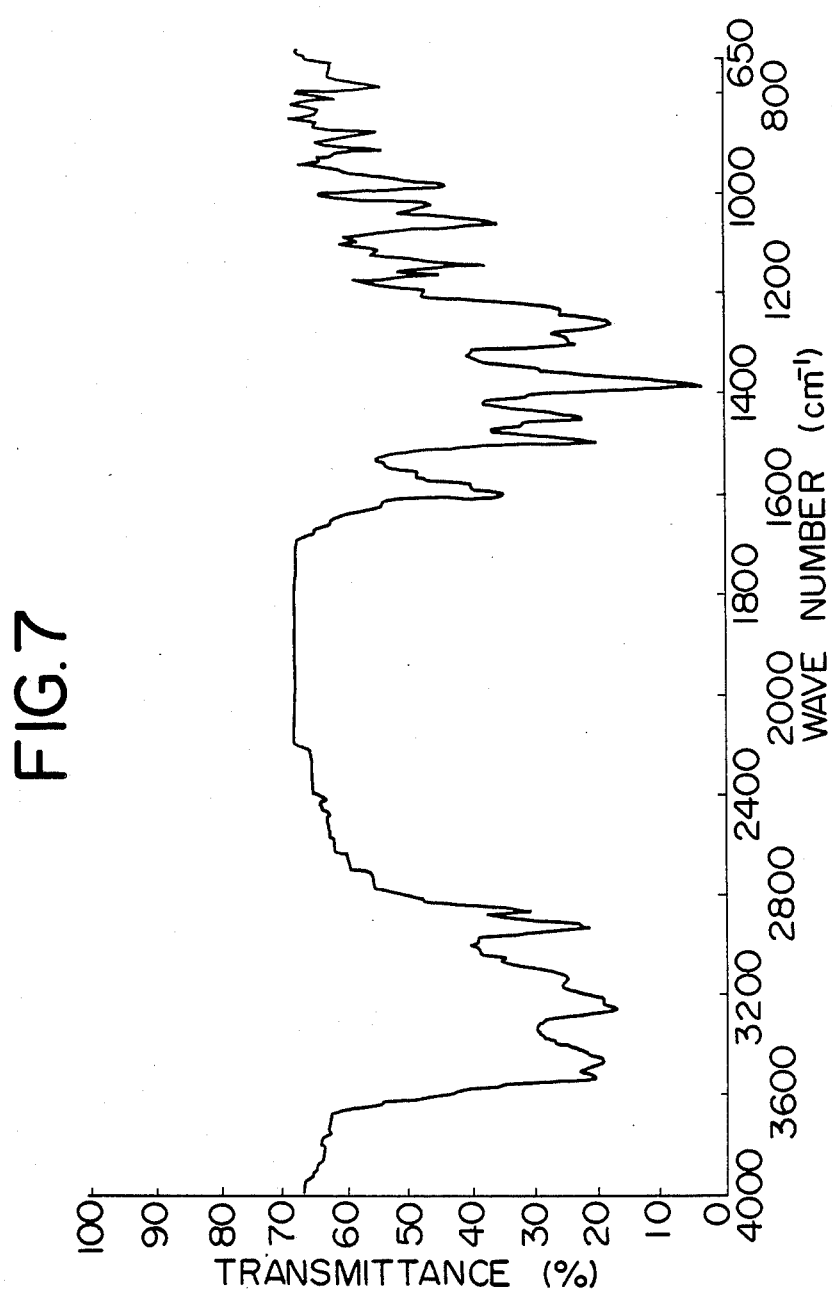
FIG. 7 shows a curve for an infrared absorption spectrum of estriol(trans-l-dach)platinum(II) complex dinitrate.
Figure 8:
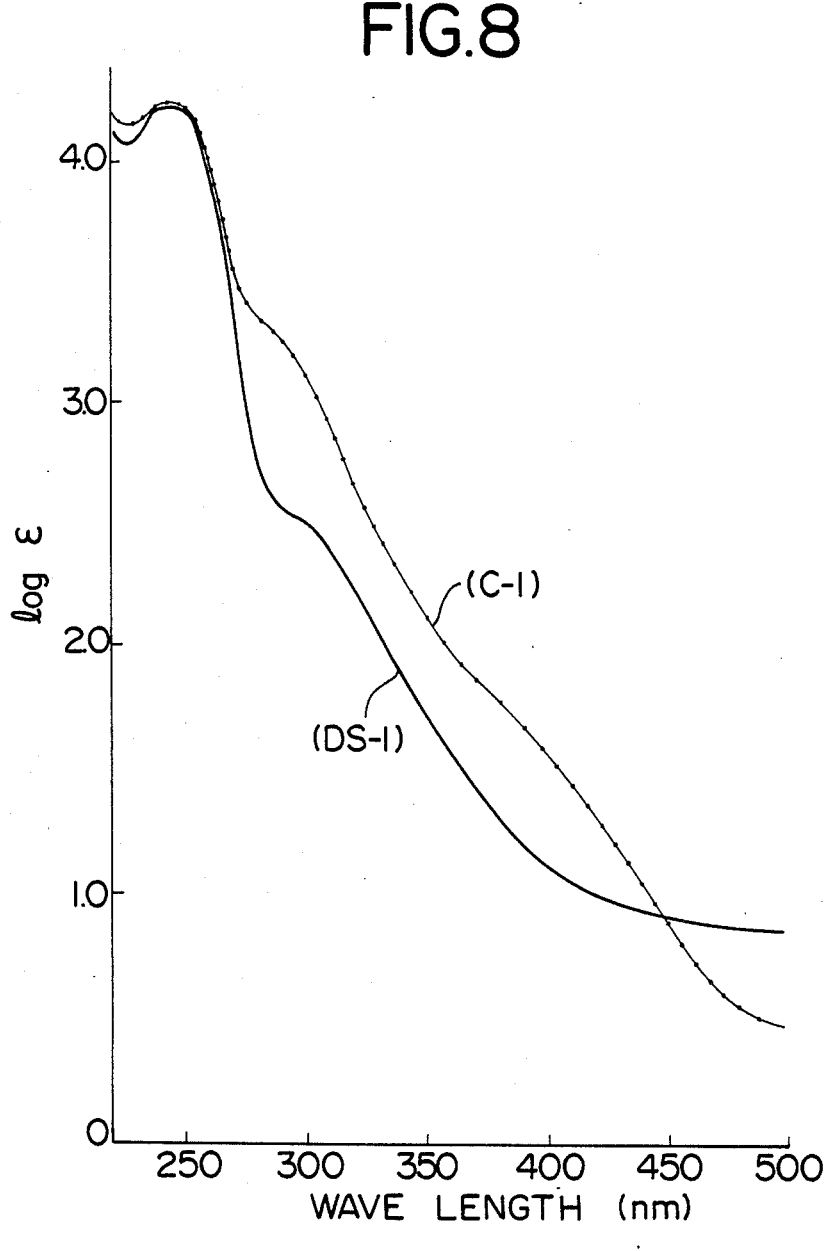
FIG. 8 shows a curve (C-1) which represents an ultraviolet absorption spectrum of hydrocortisone(trans-l-dach)platinum(II) complex dinitrate, along with a curve (DS-1) which represents the arithmetic sum of an ultraviolet absorption spectrum of the starting hydrocortisone, plus an ultraviolet absorption spectrum of the starting $(NO_3)_2$(trans-l-dach)Pt(II) complex.
Figure 9:
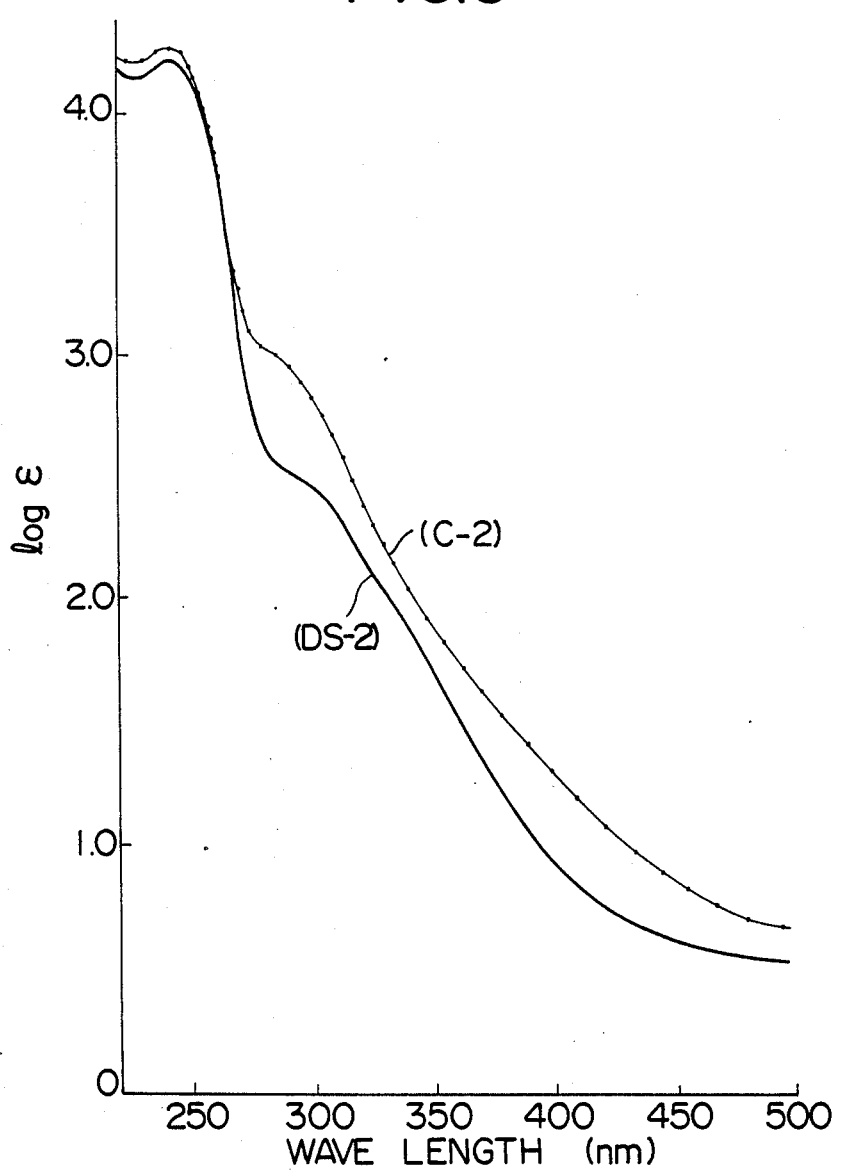
FIG. 9 shows a curve (C-2) which represents an ultraviolet absorption spectrum of cortisone-(trans-l- ultraviolet absorption spectrum of progesterone, plus an ultraviolet absorption spectrum of the starting $(NO_3)_2$(-trans-l-dach)Pt(II) complex.
Figure 10:
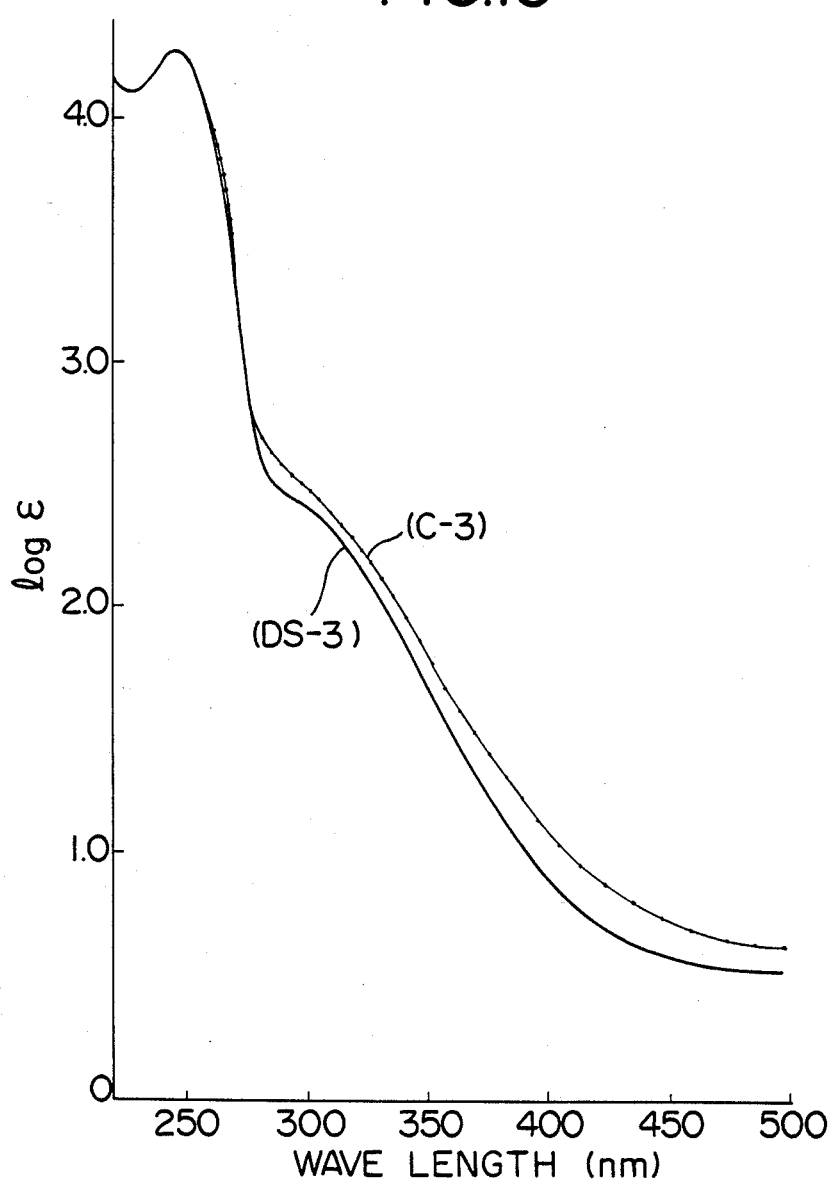

On the other hand, the logarithm values [log ($\epsilon_1+\epsilon_2$)] of the arithmetic sums of the molar absorbance index ($\epsilon_1$) of the solution of the starting platinum complexes in 50% aqueous ethanol as measured at the elapsed time of 72 hours, plus the molar absorbance index ($\epsilon_2$) of the solution of the steroids in 50% aqueous ethanol as measured at the elapsed time of 72 hours after preparation of these respective solutions are separately calculated and plotted as a function of the wave length, to draw the curves which are indicated by solid lines (DS-1, DS-2, DS-3 in FIGS. 8–10, respectively.

The details of the curves so drawn in FIGS. 8–10 are described below.

The dotted line curve (C-1) in FIG. 8 is a curve which shows logarithmic values (log $\epsilon$) of the measured absorbance index ($\epsilon$) of a platinum-steroid complex as prepared by mixing 15 ml of an aqueous solution (Solution D) of $(NO_3)_2$(trans-l-dach)platinum(II) (0.02 mol/l) with 15 ml of an ethanolic solution (Solution $S^1$) of hydrocortisone (0.02 mol/l) and then stirring the resultant mixed solution for 72 hours under light-shielded conditions. The solid line curve (D-1) in FIG. 8 is a curve which shows the logarithmic values [log ($\epsilon_1+\epsilon_2$)] of the sum of the molar absorbance index ($\epsilon_1$), which was measured after ethanol (10 ml) was added to the above solution D (10 ml), followed by stirring the resultant mixture for 72 hours under light-shielded conditions, plus the molar absorbance index ($\epsilon_2$) which was measured after water (5 ml) was added to the above Solution $S^1$ (5 ml), followed by stirring the resultant mixture for 72 hours under light-shielded conditions.

The dotted line curve (C-2) in FIG. 9 is a curve which shows the logarithmic values (log $\epsilon$) of the measured absorbance index ($\epsilon$) of a platinum-steroid complex as prepared by mixing 10 ml of an aqueous solution (Solution D) of $(NO_3)_2$ (trans-l-dach)platinum(II) (0.02 mol/l) with 10 ml of an ethanolic solution (Solution $S^2$) of cortisone (0.02 mol/l) and then stirring the resultant mixture for 72 hours under light-shielded conditions. The solid line curve (DS-2) in FIG. 9 is a curve which shows the logarithmic values [log ($\epsilon_1+\epsilon_2$)] of the sum of the molar absorbance index ($\epsilon_1$), which was measured after ethanol (10 ml) was added to the above Solution D (10 ml), followed by stirring the resultant mixture for 72 hours under light-shielded conditions, plus the molar absorbance index ($\epsilon_2$), which was measured after water (10 ml) was added to the above Solution $S^2$ (10 ml), followed by stirring the resulting mixture for 72 hours under light-shielded conditions.

The dotted line curve (C-3) in FIG. 10 is a curve which shows logarithmic values (log $\epsilon$) of the measured absorbance index ($\epsilon$) of a platinum-steroid complex as prepared by mixing 15 ml of an aqueous solution (Solution D) of $(NO_3)_2$(trans-l-dach)platinum(II) (0.02 mol/l) with 15 m of an ethanolic solution (Solution $S^3$) of progenterone (0.02 mol/l) and then stirring the resultant mixture for 72 hours under light-shielded conditions. The solid line curve (DS-3) is a curve which shows the logarithmic values [log ($\epsilon_1+\epsilon_2$)] of the sum of the molar absorbance index ($\epsilon_1$), which was measured after ethanol (10 ml) was added to the above Solution D (10 ml), followed by stirring the resulting mixture for 72 hours under light-shielded conditions, plus the molar absorbance index ($\epsilon_2$), which was measured after water (5 ml) was added to the above Solution $S^3$ (5 ml), followed by stirring the resultant mixture for 72 hours under light-shielded conditions.

(B) Variation in the absorbance index at 290 nm with passage of time:

It is the UV absorption as measured at 290 nm that the UV absorption value of a platinum-steroid complex varies most markedly depending on the kind of the steroid.

Variation in the molar absorbance index (ε) at 290 nm of the platinum-steroid complex, which was formed by mixing the ethanolic solution of a steroid compound with the aqueous solution of the starting platinum complex, was hence measured and plotted against the passage of time (in hours) lapsed after the mixing of said ethanolic solution with said aqueous solution. The variations so measured are shown as three curves in FIG. 11 for the hydrocortisone-platinum(II) complex, the cortisone-platinum(II) complex and the progesterone-platinum(II) complex as formed.

(C) Measurement of pH variations with passage of time:

An ethanolic solution (5 ml) of hydrocortisone (0.02 mol/l) was mixed with 5 ml of an aqueous solution of the starting platinum complex (0.02 mol/l). The pH of the resultant mixture solution was measured by a pH meter immediately after the mixing, and at times of 24 hours later, 48 hours later and 69 hours later.

| Time | pH |
|---|---|
| Immediately after the mixing | 3.30 |
| 24 hrs. later | 2.84 |
| 48 hrs. later | 2.76 |
| 69 hrs. later | 2.67 |

The pH of the aqueous solution of the starting platinum complex (0.02 mol/l) amounted to 2.93.

Now, when a comparison is made between the dotted line curve and the corresponding solid line curve as shown in each of FIGS. 8-10, it is seen that the platinum-steroid complexes have greater values of the UV absorption in a wave length range of 280 nm-450 nm$^-$ than the total UV absorptions of the starting materials. It is hence contemplated that the solutions, which had been prepared by mixing the ethanolic steroid solution with the aqueous solution of $(NO_3)_2$(trans-l-dach)Pt(II) complex and of which the UV absorption spectrum was measured in term of the absorbance index (ε), were each not a simple mixture of the starting materials as mixed together, but the starting materials had interacted with each other in said solution.

From FIG. 11, it is observed that progesterone which contains no hydroxyl groups (or oxo group O=) at the 11-position or 17-position did not undergo any substantial changes in the absorbance index (ε) with the passage of time. A comparison in FIG. 11 between the hydrocortisone-platinum complex and the cortisone-platinum complex reveals that the complex of the hydrocortisone containing a hydroxyl group at the 11-position underwent greater changes in the absorbance index than the complexes of the other steroid compounds.

The variations in the pH were also investigated, when it is seen that the pH dropped down with the passage of time. This seems to mean that the protons of the hydroxyl groups at the 11- and 17-positions takes part in the complexing reaction. In view of the fact that no substantial variations was observed to take place at the maximum wave length, however, it appears that the bonds between the platinum atom and steroid compound are not very strong, and the variation of UV absorption was involved due to the weak interaction and the co-ordination bond which incured between the starting platinum complex and steroid compound.

In order to ascertain that these variations as above were not caused due to the withdrawal of the protons from the hydroxyl groups of each steroid compound, aqueous solutions of the respective steroid compounds were separately stirred in the presence of sodium hydroxide under alkaline conditions, and UV absorption spectra of the stirred aqueous solutions were measured.

(D) Variations in the UV absorbance index occurring upon reaction of hydroxyl anion and sodium cation with steroid compounds:

The hydroxyl anion and sodium cation were reacted with steroid compound by mixing as follows:
Hydrocortisone+water+0.15N NaOH
Cortisone+water+0.15N NaOH
Progesterone+water+0.15N NaOH A solution of each steroid compound (0.02 mol/l) was mixed with 0.15N aqueous NaOH, and an UV absorption spectrum of the resultant mixture was determined periodically with the passage of time, in term of the absorbance index (ε) as measured at 290 nm, and in the same way as in the above-described measurement of the UV absorbance index of the platinum-steroid complex. In order to investigate the variation in the absorbance index at 290 nm of the reaction solution containing sodium hydroxide and each steroid with the passage of time, the measured variation in the absorbance index at 290 nm is diagrammatically represented by the curves as shown in FIG. 12, in the same manner as for the platinum-steroid complex. Similarly, the time-dependent variation in the absorbance index (ε) of said reaction solution containing sodium hydroxide and each steroid compound as measured in the visible wave length region (at 370 nm for progesterone and hydrocortisone; and at 420 nm for cortisone) was determined and is diagrammatically represented by the curves as shown in FIG. 13.

Incidentally, steroid compounds having a hydroxyl group at the 17-position usually show a chelate structure as shown by the following formula:

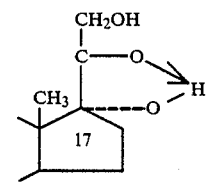

They are known to form complexes with $Zn^{2+}$, $Cu^{2+}$ and the like.

In the platinum(II)-steroid complexes of the present invention, it appears that a steroid compound having a 17-hydroxyl group such as cortisone or hydrocortisone undergoes a reaction with the platinum atom and develops a yellow color but does not effect withdrawal of the proton from said hydroxyl group.

What we claim is:

1. An antitumor platinum(II)-steroid complex represented by the general formula (I)

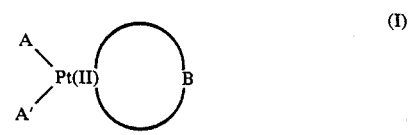

wherein A and A' taken together form a 1,2-cyclohexanediamine ligand of the formula:

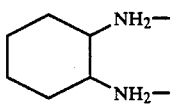

where the 1- and 2-amino groups have a configuration selected from cis-, trans-l- and trans-d-, relative to the cyclohexane ring; or A and A' taken together form a 2-(aminomethyl)cyclohexylamine ligand of the formula:

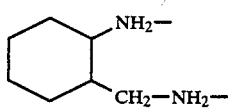

where the 1-amino group and 2-aminomethyl group have a configuration selected from cis-l-, cis-d-, trans-l- and trans-d-, or a mixture thereof, relative to the cyclohexane ring; or A and A' taken together form an ethylenediamine ligand of the formula:

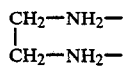

or A and A' each denote a group $NH_3$—, and B denotes a steroid compound which coordinates the platinum(II) atom and is selected from the group consisting of cortisone, hydrocortisone, prednisone, prednisolone, methylprednisone, methylprednisolone, 17-α-hydroprogesterone, estrone, estriol, progestrone, cholic acid, deoxycholic acid, androsterone, testosterone and testosterone propionate, or a nitrate of the platinum(II)-steroid complex of the formula (I).

2. A platinum (II)-steroid complex of claim 1 in which A and A' taken together form a ligand selected from cis-1,2-cyclohexanediamine, trans-d-1,2-cyclohexanediamine, and trans-l-1,2-cyclohexanediamine; and B is a steroid compound.

3. A platinum (II)-steroid complex of claim 1 in which A and A' taken together form a ligand selected from cis-dl-2-(aminomethyl)cyclohelamine and trans-dl-2-(aminomethyl) cyclohexylamine; and B is a steroid compound.

4. Cortisone-(trans-l-1,2-cyclohexanediamine)-platinum(II) complex dinitrate.

5. Hydrocortisone-(trans-l-1,2-cyclohexanediamine) platinum(II) complex dinitrate 6. Methylprednisolone-(trans-l-1,2-cyclohexanediamine) platinum(II) complex dinitrate 7. Prednisolone-(cis-dl-2-aaminomethyl)cyclohexylamine) platinum(II) complex dinitrate.

8. 17-α-hydroxyprogesterone-(trans-l-1,2-cyclohexanediamine)platinum(II) complex dinitrate.

9. Progesterone-(trans-l-1,2-cyclohexanediamine) platinum(II) complex dinitrate.

* * * * *